United States Patent [19]

Katsube et al.

[11] 4,012,515
[45] Mar. 15, 1977

[54] ARYL KETONES AND PRODUCTION THEREOF

[75] Inventors: Junki Katsube; Masaru Nakao; Kikuo Sasajima, all of Toyonaka; Isamu Maruyama; Masaharu Takayama, both of Minoo; Keiichi Ono, Nishinomiya; Shigenari Katayama, Takarazuka; Yoshihiro Tanaka, Takarazuka; Shigeho Inaba, Takarazuka; Hisao Yamamoto, Kobe, all of Japan

[73] Assignee: Sumitomo Chemical Company, Limited, Japan

[22] Filed: July 29, 1975

[21] Appl. No.: 600,119

Related U.S. Application Data

[63] Continuation-in-part of Ser. No. 316,026, Dec. 18, 1972, Pat. No. 3,922,266.

[52] U.S. Cl. ............................ 424/267; 260/240 R
[51] Int. Cl.$^2$ ......................................... C07D 211/52
[58] Field of Search ................ 260/240 R; 424/267

[56] References Cited
UNITED STATES PATENTS 3,922,266  11/1975  Katsube et al. ............... 424/267

*Primary Examiner*—Henry R. Jiles
*Assistant Examiner*—C. M. S. Jaisle
*Attorney, Agent, or Firm*—Craig & Antonelli

[57] ABSTRACT

Novel olefinic aryl ketone compounds of the formula:

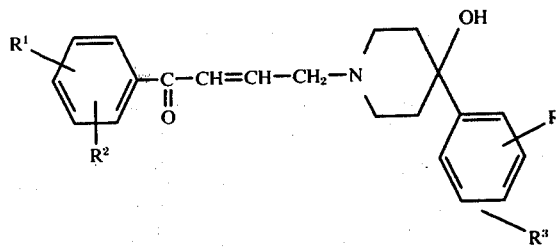

wherein $R^1$ is hydrogen, halogen, $C_{1-4}$ alkyl, or $C_{1-4}$ alkoxy, $R^2$ is hydrogen or halogen, and $R^3$ and $R^4$ are each hydrogen, halogen, $C_{1-4}$ alkyl or trifluoromethyl, and their non-toxic salts, which possess various useful pharmacological activities and can be produced by reaction of an acetylenic alcohol of the formula:

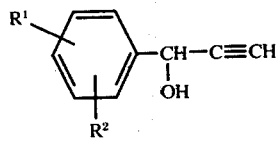

wherein $R^1$ and $R^2$ are each as defined above, with formaldehyde and an amine of the formula:

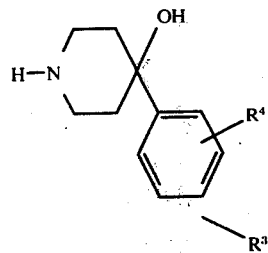

wherein $R^3$ and $R^4$ are each as defined above; reduction of the resultant acetylenic aryl alcohol; and oxidation of the resultant olefinic aryl alcohol.

6 Claims, No Drawings

ARYL KETONES AND PRODUCTION THEREOF

This is a continuation-in-part application of our co-pending application Ser. No. 316,026, filed on Dec. 18, 1972 now U.S. Pat. No. 3,922,266, patented Nov. 25, 1975.

The present invention relates to novel olefinic aryl ketone derivatives and their production and use.

The novel olefinic aryl ketone derivatives provided by this invention are olefinic aryl ketone compounds of the formula:

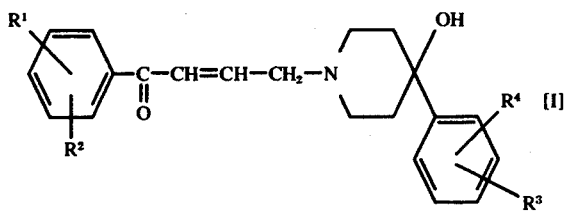

wherein $R^1$ is hydrogen, halogen, $C_{1-4}$ alkyl, or $C_{1-4}$ alkoxy, $R^2$ is hydrogen or halogen, and $R^3$ and $R^4$ are each hydrogen, halogen, $C_{1-4}$ alkyl, or trifluoromethyl, and their non-toxic salts.

In the significances mentioned as above, $C_{1-4}$ alkyl includes methyl, ethyl, n-propyl, etc.; $C_{1-4}$ alkoxy includes methoxy, ethoxy, n-propoxy, etc.; and halogen includes fluorine, chlorine, and bromine.

Among the olefinic aryl ketones [I] of the invention, the compounds of the following formula are preferable:

wherein $R^3$ and $R^4$ are each as defined above.

Specific examples of such olefinic aryl ketones [I] are as follows:

1-[4-(p-Fluorophenyl)-4-oxo-2-butenyl]-4-(p-chlorophenyl)-4-hydroxypiperidine;
1-[4-(p-Fluorophenyl)-4-oxo-2-butenyl[-4-(m-trifluoromethylphenyl)-4-hydroxypiperidine;
1-[4-(p-Fluorophenyl)-4-oxo-2-butenyl]-4-(p-toluyl)-4-hydroxypiperidine;
1-[4-(p-Fluorophenyl)-4-oxo-2-butenyl]-4-(m-chloro-p-toluyl)-4-hydroxypiperidine;
1-[4-(p-Fluorophenyl)-4-oxo-2-butenyl]-4-(m-trifluoromethyl-p-chlorophenyl)-4-hydroxypiperidine;
1-[4-(p-Fluorophenyl)-4-oxo-2-butenyl]-4-(3,4-dichlorophenyl)-4-hydroxypiperidine, etc.

The olefinic aryl ketones [I] can form acid addition salts, of which examples are hydrochloride, hydrobromide, acetate, oxalate, citrate, tartrate, succinate, fumarate, maleate, lactate, etc.

The olefinic aryl ketones [I] and their non-toxic salts possess a variety of useful pharmacological activities and therefore they are useful as medicines. That is, these olefinic aryl ketones [I] all possess potent central nervous system depressive activities, and therefore these compounds are useful as neuroleptics.

It is already known that the corresponding aryl ketones of the formula:

wherein $R^1$, $R^2$, $R^3$, and $R^4$ are each as defined above, show excellent central nervous system depressive effects, and some of them have already been put to practical use as neuroleptics. For instance, British Pat. No. 881,893 discloses γ-(4-hydroxy-4-phenylpiperidino)-butyrophenones and their use as central nervous system depressants.

The olefinic aryl ketones [I], however, have been found to exhibit the same degree of or more potent central nervous system depressive activity compared with the corresponding aryl ketones [A], and such central nervous system depressive effects may be verified by the several known pharmacological methods, for instance, by antiapomorphine test, etc.

Furthermore, the olefinic aryl ketones [I] have been found to possess potent anti-acetylcholine effects. It is well knwon that the aryl ketones [A] frequently produces extrapyramydal side-effects [cf. P. A. J. Janssen et al.: Arzneim, Forsch., 15, 104 (1965)], and these symptoms are antagonized by using anti-acetylcholine drugs (anti-parkinson drugs) [cf. C. Morpurgo et al.: Psychopharmacologia, 6, 178 (1964)].

In view of the above mentioned pharmacological profile, the olefinic aryl ketones [I] have more favorable features as neuroleptics; potent neuroleptics without producing extrapyramydal side-effects.

Thus, the olefinic aryl ketones [I] are not only useful as neuroleptics by itself but also useful as intermediates for other drugs such as the aryl ketones [A].

Each of the olefinic aryl ketones [I] and their non-toxic salts may be brought into a form suitable for administration according to a method known per se. For the preparation of pharmaceutical compositions, they may be mixed with carriers, diluents, lubricants, fillers and/or binders such as lactose, sucrose, calcium phosphate, starch, talcum, casein, magnesium stearate, methyl cellulose, polyglycols, tragacanth and the like, sometimes together with stabilizers and emulsifying agents. The resulting mixture may be processed in a usual manner to tablets, capsules, pills, ampoules and the like. The usual oral dosage of the active ingredient is between about 0.1 mg and about 1000 mg daily, preferably from 1 mg to 100 mg per day.

According to the present invention, the olefinic aryl ketones [I] and the intermediates as above mentioned can be produced by the reaction pathway as shown in the following scheme:

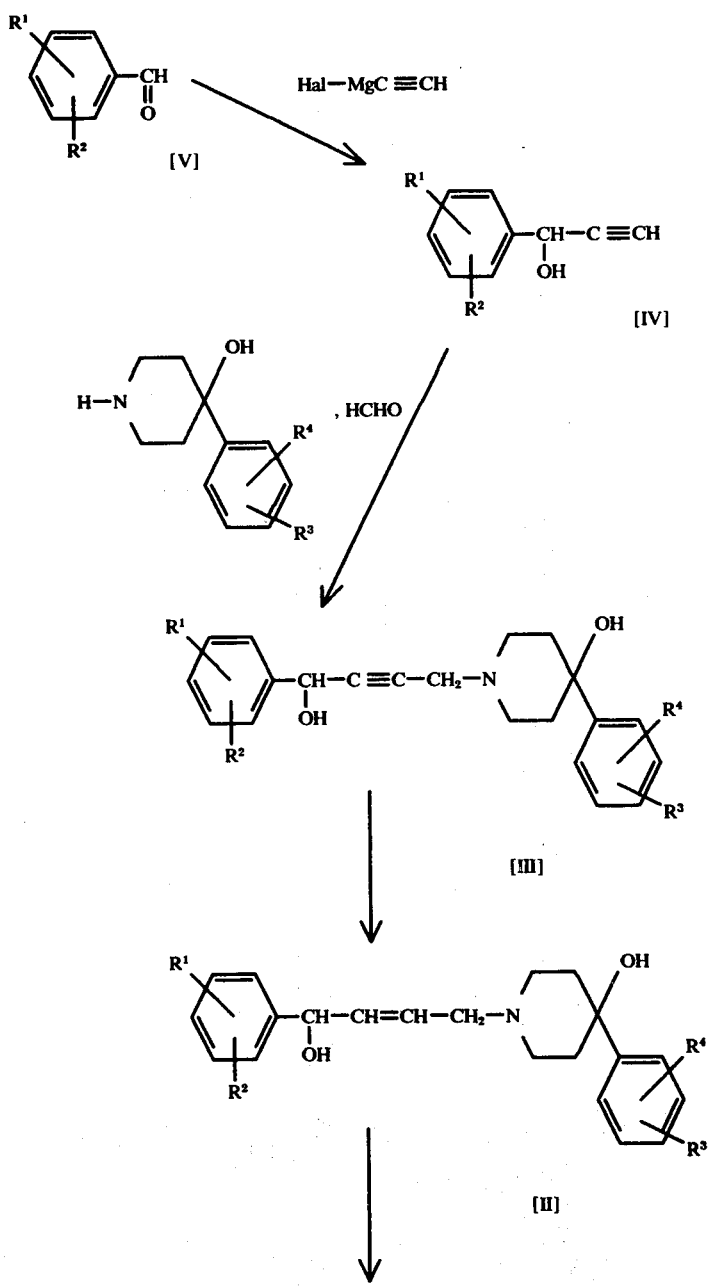

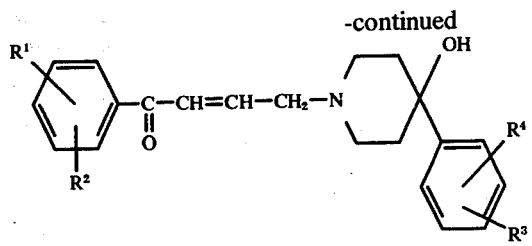 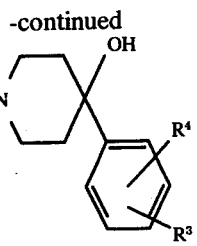

[I]

wherein Hal represents a halogen atom and $R^1$, $R^2$, $R^3$, and $R^4$ are each as defined above.

The reactions in the above scheme will be hereinafter described step by step in details.

Firstly, the acetylenic aryl alcohol [III] may be prepared by reacting the acetylenic alcohol [IV] with an amine of the formula:

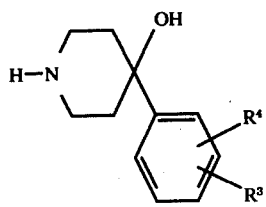

wherein $R^3$ and $R^4$ are each as defined above in the presence of formaldehyde.

The reaction is favorably carried out in the presence of a catalyst in an inert solvent around room temperature or below, or under reflux conditions. Examples of the solvent are water, methanol, ethanol, isopropanol, isoamyl alcohol, diethyl ether, tetrahydrofuran, dioxane, diethyleneglycol dimethyl ether, ethyleneglycol monomethyl ether, etc. As the catalyst, there are exemplified cupric chloride, cuprous chloride, cupric sulfate, cuprous acetate, ferric chloride, etc.

In the above reaction, the starting acetylenic alcohol [IV] may be replaced by any obvious chemical equivalent such as a compound of the formula:

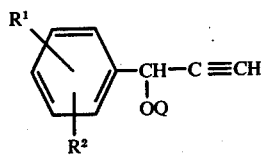

[IV']

wherein Q is a conventional protective group for hydroxyl such as tetrahydropyranyl, t-butyl, benzyl, acetyl or benzoyl and $R^1$ and $R^2$ are each as defined above.

The said acetylenic alcohol [IV] is obtainable by reacting the benzaldehyde [V] with a Grignard reagent of the formula:

Hal—MgC≡CH wherein Hal is as defined above according to a conventional procedure.

The acetylenic aryl alcohol [III] is then reduced to the olefinic aryl alcohol [II].

This reduction may be conducted by a conventional semihydrogenation technique. Thus, the semihydrogenation is conveniently carried out in an alcoholic solvent in the presence of a catalyst (e.g. Lindlar catalyst, palladium on barium sulfate deactivated with quinoline) around room temperature or below. When an equimolar amount of hydrogen is absorbed, the reaction is substantially completed, and the desired product is obtained in a good yield.

The said reduction may be also accomplished by reacting the acetylenic aryl alcohol [III] with a reducing agent such as a metal hydride (e.g. lithium aluminum hydride, sodium borohydride) or the combination of an alkali metal and an amine (e.g. sodium in liquid ammonia, lithium in methylamine). The reaction using the metal hydride is ordinarily carried out in an inert solvent (e.g. diethylether, tetrahydrofuran, dioxane, ethyleneglycol dimethylether, benzene, toluene, hexane, cyclohexane) at a temperature from about 0° C to a refluxing temperature. The recovery of the desired product from the reaction mixture may be effected by a usual manner.

The olefinic aryl alcohol [II] thus obtained possesses a cis- or trans-olefinic double bond. One of the cis- and trans-isomers can be produced selectively by the choice of a suitable reduction procedure. For instance, the catalytic hydrogenation affords usually the cis-isomer and the reduction with a metal hydride gives ordinarily the trans-isomer.

The olefinic aryl alcohol [III] is then oxidized to the olefinic aryl ketone [II].

The oxidation may be carried out by treating the olefinic aryl alcohol [III] with an oxidizing agent (e.g. manganese dioxide, chromic acid, chromates, permanganates, oxygen, dimethylsulfoxide, peracids), usually in water or an organic solvent at room temperature or under cooling or gentle heating. The reaction product is readily separated from the reaction mixture by a conventional procedure.

The olefinic aryl ketones [I] thus obtained may be converted into their acid addition salts by usual manners, and reconversion from the acid addition salts to the original free bases may be also carried out by ordinary manners.

Practical and presently preferred embodiments of the present invention are illustratively shown in the following Examples wherein abbreviations have each a conventional meaning. These Examples should not be construed as limiting the scope of the invention.

EXAMPLE 1

To a solution of 4-(p-chlorophenyl)-4-hydroxypiperidine (4.00 g) in a mixture of dioxane (30 ml), water (10 ml), and 37% formalin (2.06 g), there were added a solution of 3-(p-fluorophenyl)-3-hydroxy-1-propyne (2.38 g) in dioxane (5 ml) and a solution of cupric sulfate pentahydrate (127 mg) in water (4 ml) under ice-cooling. The resulting mixture was heated at 80° C for 2 hours and, after cooling, the resulting mixture was filtered and the filtrate was concentrated under reduced pressure and extracted with chloroform. The chloroform extracts were dried over magnesium sulfate. After evaporation of the solvent, the residual oil was chromatographed on silica gel to afford 1-[4-(p-fluorophenyl)-4-hydroxy-2-butynyl]-4-(p-chlorophenyl)-4-hydroxypiperidine (4.56 g) as white crystals, M.P. 145° – 146.2° C.

In the same manner as above, the following compounds were obtained:

1-[4-(p-Fluorophenyl)-4-hydroxy-2-butynyl]-4-(m-trifluoromethylphenyl)-4-hydroxypiperidine, $\nu_{OH}^{neat}$ 3350 cm$^{-1}$;

1-[4-(p-Fluorophenyl)-4-hydroxy-2-butynyl]-4-(p-toluyl)-4-hydroxypiperidine, $\nu_{OH}^{neat}$ 3320 cm$^{-1}$;

1-[4-(p-Fluorophenyl)-4-hydroxy-2-butynyl]-4-(m-chloro-p-toluyl)-4-hydroxypiperidine, $\nu_{OH}^{neat}$ 3350 cm$^{-1}$;

1-[4-(p-Fluorophenyl)-4-hydroxy-2-butynyl]-4-(m-trifluoromethyl-p-chlorophenyl)-4-hydroxypiperidine, $\nu_{OH}^{neat}$ 3300 cm$^{-1}$;

1-[4-(p-Fluorophenyl)-4-hydroxy-2-butynyl]-4-(3,4-dichlorophenyl)-4-hydroxypiperidine, $\nu_{OH}^{neat}$ 3360 cm$^{-1}$.

EXAMPLE 2

To an ethereal solution (14 ml) of lithium aluminum hydride (0.37 g) was added a solution of 1-[4-(p-fluorophenyl)-4-hydroxy-2-butynyl]-4-(p-chlorophenyl)-4-hydroxypiperidine (1.20 g) in ether (13 ml) under ice-cooling. After stirring at 10° C for 1.5 hours and further at 25° C for 4 hours, acetone was added thereto in order to consume excess of lithium aluminum hydride. The resulting mixture was poured into an aqueous ammonium chloride solution and extracted with ethyl acetate. The ethyl acetate extracts were washed with water, dried over anhydrous magnesium sulfate and concentrated to afford 1-[4-(p-fluorophenyl)-4-hydroxy-2-butenyl]-4-(p-chlorophenyl)-4-hydroxypiperidine (1.50 g) as white needles, M.P. 149° – 151° C.

In the same manner as above, the following compounds were obtained:

1-[4-(p-Fluorophenyl)-4-hydroxy-2-butenyl]-4-(m-trifluoromethylphenyl)piperidine, M.P. 126° – 127° C;

1-[4-(p-Fluorophenyl)-4-hydroxy-2-butenyl]-4-(p-toluyl)-4-hydroxypiperidine, $\nu_{OH}^{neat}$ 3325 cm$^{-1}$;

1-[4-(p-Fluorophenyl)-4-hydroxy-2-butenyl]-4-(m-chloro-p-toluyl)-4-hydroxypiperidine, M.P. 108° – 110° C;

1-[4-(p-Fluorophenyl)-4-hydroxy-2-butenyl]-4-(m-trifluoromethyl-p-chlorophenyl)-4-hydroxypiperidine, $\nu_{OH}^{neat}$ 3320 cm$^{-1}$;

1-[4-(p-Fluorophenyl)-4-hydroxy-2-butenyl]-4-(3,4-dichlorophenyl)-4-hydroxypiperidine, $\nu_{OH}^{neat}$ 3360 cm$^{-1}$.

EXAMPLE 3

A mixture of 1-[4-(p-fluorophenyl)-4-hydroxy-2-butenyl]-4-(p-chlorophenyl)-4-hydroxypipieridine (1.50 g) in chloroform (50 ml) and manganese dioxide (7.0 g) was stirred for 1 hour under ice-cooling. Filtration of inorganic materials and concentration of the filtrate afforded 1-[4-(p-fluorophenyl)-4-oxo-2-butenyl]-4-(p-chlorophenyl)-4-hydroxypiperidine (1.24 g) as pale yellow needles, M.P. 111.5° – 113° C.

In the same manner as above, the following compounds were obtained:

1-[4-(p-Fluorophenyl)-4-oxo-2-butenyl]-4-(m-trifluoromehtylphenyl)-4-hydroxypiperidine, M.P. 97° – 97.5° C;

1-[4-(p-Fluorophenyl)-4-oxo-2-butenyl]-4-(p-toluyl)-4-hydroxypiperidine;

1-[4-(p-Fluorophenyl)-4-oxo-2-butenyl]-4-(m-chloro-p-toluyl)-4-hydroxypiperidine, M.P. 113° – 115° C;

1-[4-(p-Fluorophenyl)-4-oxo-2-butenyl]-4-(m-trifluoromethyl-p-chlorophenyl)-4-hydroxypiperidine;

1-[4-(p-Fluorophenyl)-4-oxo-2-butenyl]-4-(3,4-dichlorophenyl)-4-hydroxypiperidine.

What is claimed is:

1. An olefinic aryl ketone of the formula:

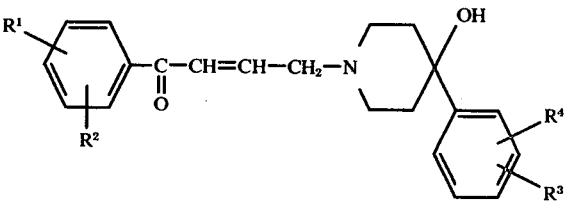

wherein $R^1$ is fluorine, $R^2$ is hydrogen, and $R^3$ and $R^4$ are each hydrogen, halogen, $C_{1-4}$ alkyl or trifluoromethyl, and its non-toxic salt.

2. An olefinic aryl ketone of the formula:

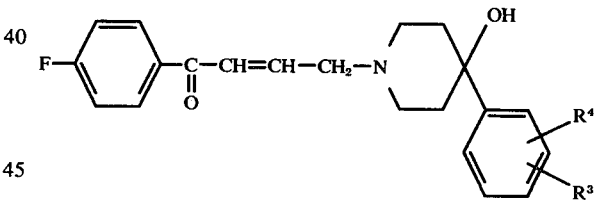

wherein $R^3$ and $R^4$ are each hydrogen, halogen, $C_{1-4}$ alkyl, or trifluoromethyl, and its non-toxic salt.

3. A process for producing an olefinic aryl ketone of the formula:

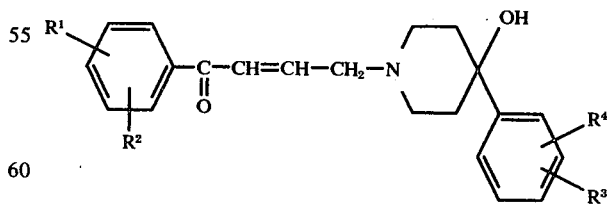

wherein $R^1$ is hydrogen, halogen, $C_{1-4}$ alkyl, or $C_{1-4}$ alkoxy, $R^2$ is hydrogen or halogen, and $R^3$ and $R^4$ are each hydrogen, halogen, $C_{1-4}$ alkyl or trifluoromethyl, and its non-toxic salt, which comprises oxidizing an olefinic aryl alcohol of the formula:

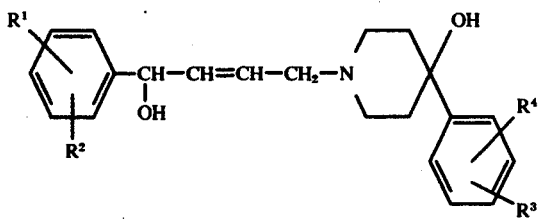

wherein $R^1$, $R^2$, $R^3$, and $R^4$ are each as defined above, or its non-toxic salt.

4. A process for producing an olefinic aryl ketone of the formula:

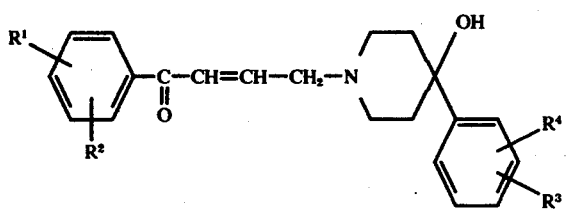

wherein $R^1$ is hydrogen, halogen, $C_{1-4}$ alkyl, or $C_{1-4}$ alkoxy, $R^2$ is hydrogen or halogen, and $R^3$ and $R^4$ are each hydrogen, halogen, $C_{1-4}$ alkyl or trifluoromethyl, and its non-toxic salts, which comprises reducing an acetylenic aryl alcohol of the formula:

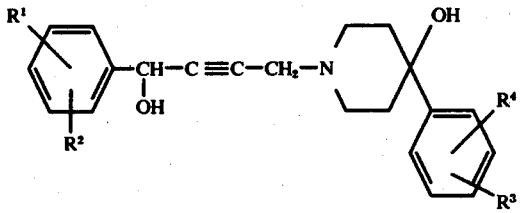

wherein $R^1$, $R^2$, $R^3$, and $R^4$ are each as defined above, or its non-toxic salt and oxidizing the resltant olefinic aryl alcohol of the formula:

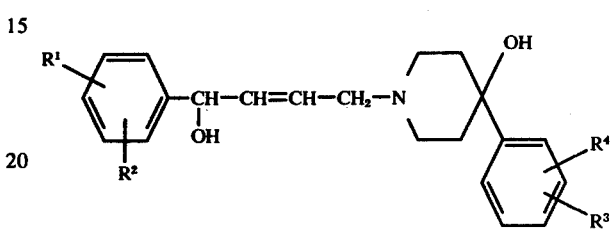

wherein $R^1$, $R^2$, $R^3$, and $R^4$ are each as defined above, or its non-toxic salt.

5. A neuroleptic composition comprising an effective amount of the olefinic aryl ketone according to claim 1, or its non-toxic salt and a pharmaceutically acceptable carrier.

6. A method for inducing a neuroleptic effect in an animal comprising administering an effective amount of the olefinic aryl ketone according to claim 1, and its non-toxic salt as medicines.

* * * * *